(12) United States Patent
Skold

(10) Patent No.: US 7,169,618 B2
(45) Date of Patent: Jan. 30, 2007

(54) MAGNETIC PARTICLES AND METHODS OF PRODUCING COATED MAGNETIC PARTICLES

(75) Inventor: Carl Nelson Skold, Mountain View, CA (US)

(73) Assignee: Skold Technology, Mountain View, CA (US)

( * ) Notice: Subject to any disclaimer, the term of this patent is extended or adjusted under 35 U.S.C. 154(b) by 76 days.

(21) Appl. No.: 09/891,787

(22) Filed: Jun. 26, 2001

(65) Prior Publication Data

US 2002/0000398 A1    Jan. 3, 2002

Related U.S. Application Data

(60) Provisional application No. 60/214,657, filed on Jun. 28, 2000.

(51) Int. Cl.
*G01N 33/553* (2006.01)
*A61K 51/00* (2006.01)

(52) U.S. Cl. ............ 436/526; 436/525; 436/536; 436/541; 436/538; 436/544; 436/806; 436/149; 436/151; 436/530; 424/1.1

(58) Field of Classification Search ............ 436/526, 436/525, 536, 538, 541, 544, 806, 149, 151, 436/161, 530; 424/1.1
See application file for complete search history.

(56) References Cited

U.S. PATENT DOCUMENTS

| | | | |
|---|---|---|---|
| 3,970,518 A | 7/1976 | Giaever | |
| 4,018,886 A | 4/1977 | Giaever | |
| 4,048,298 A * | 9/1977 | Niswender | |
| 4,101,435 A | 7/1978 | Hasegawa | |
| 4,157,323 A | 6/1979 | Yen | |
| 4,208,294 A | 6/1980 | Khalafalla | |
| 4,230,685 A | 10/1980 | Senyei | |
| 4,267,235 A | 5/1981 | Rembaum | |
| 4,329,241 A | 5/1982 | Massart | |
| 4,358,388 A | 11/1982 | Daniel | |
| 4,411,891 A | 10/1983 | Mizutani et al. | |
| 4,452,773 A | 6/1984 | Molday | |
| 4,554,088 A | 11/1985 | Whitehead | |
| 4,628,037 A * | 12/1986 | Chagnon et al. | |
| 4,654,267 A | 3/1987 | Ugelstad | |
| 4,672,040 A * | 6/1987 | Josephson | |
| 4,695,392 A | 9/1987 | Whitehead et al. | |
| 4,695,393 A | 9/1987 | Whitehead et al. | |
| 4,698,302 A | 10/1987 | Whitehead et al. | |
| 4,770,183 A | 9/1988 | Groman et al. | |
| 4,795,698 A | 1/1989 | Owen | |
| 4,827,945 A | 5/1989 | Groman | |
| 4,904,256 A | 2/1990 | Yamaguchi | |
| 4,935,147 A | 6/1990 | Ullman | |
| 4,951,675 A | 8/1990 | Groman et al. | |
| 5,055,288 A | 10/1991 | Lewis et al. | |
| 5,069,216 A | 12/1991 | Groman et al. | |
| 5,102,652 A | 4/1992 | Groman et al. | |
| 5,141,739 A | 8/1992 | Jung et al. | |
| 5,160,726 A | 11/1992 | Josephson et al. | |
| 5,164,297 A | 11/1992 | Josephson et al. | |
| 5,204,457 A | 4/1993 | Maruno | |
| 5,219,554 A | 6/1993 | Groman et al. | |
| 5,225,282 A * | 7/1993 | Chagnon et al. | |
| 5,248,492 A | 9/1993 | Groman et al. | |
| 5,254,460 A | 10/1993 | Josephson et al. | |
| 5,262,176 A | 11/1993 | Palmacci | |
| 5,284,646 A | 2/1994 | Menz et al. | |
| 5,314,679 A | 5/1994 | Lewis et al. | |
| 5,328,681 A * | 7/1994 | Kito et al. ............ 424/9.322 |
| 5,336,506 A | 8/1994 | Josephson et al. | |
| 5,342,607 A | 8/1994 | Josephson | |
| 5,349,957 A * | 9/1994 | Yudelson | |
| 5,352,432 A | 10/1994 | Menz et al. | |
| 5,395,688 A * | 3/1995 | Wang et al. | |
| 5,411,863 A | 5/1995 | Miltenyi | |
| 5,424,419 A | 6/1995 | Hasegawa et al. | |
| 5,478,576 A | 12/1995 | Jung et al. | |
| 5,490,991 A | 2/1996 | Enriquez et al. | |
| 5,492,814 A * | 2/1996 | Weissleder | |
| 5,512,332 A | 4/1996 | Liberti | |
| 5,512,439 A | 4/1996 | Hornes | |
| 5,554,386 A | 9/1996 | Groman et al. | |
| 5,589,591 A | 12/1996 | Lewis | |
| 5,597,531 A | 1/1997 | Liberti | |
| 5,679,323 A | 10/1997 | Menz et al. | |
| 5,766,572 A | 6/1998 | Hasegawa et al. | |
| 5,776,360 A * | 7/1998 | Sieber | |

(Continued)

OTHER PUBLICATIONS

Bo Johnsson, Stefan Lofas, and Gabrielle Lindquist, Analytical Biochemistry, 198,268-277 (1991).

N.D. Heindel, M.A.Kauffman, E.K.Akyea, S.A. Engel, M.F. Frey, C.J. Lacey, and R.A. Egolf, Bioconjugate Chemistry, 5, 98-100, (1994).

(Continued)

*Primary Examiner*—Long V. Le
*Assistant Examiner*—Pensee T. Do
(74) *Attorney, Agent, or Firm*—Kolisch Hartwell, P.C.

(57) ABSTRACT

An improved method for separating materials is provided, using colloidal, magnetizable aggregates, optionally silanized, and coated with a one or more layers of novel polysaccharide derivatives. Materials separated by the aggregates of the invention include inorganic and organic molecules, viruses, organelles, and cells. The invention also relates to a kit for separating such materials. The separated materials are useful in analytical and preparative or in diagnostic and therapeutic techniques.

19 Claims, No Drawings

U.S. PATENT DOCUMENTS

| | | | |
|---|---|---|---|
| 5,855,790 A | * | 1/1999 | Bradbury et al. ........... 210/676 |
| 5,981,507 A | | 11/1999 | Josephson et al. |
| 5,985,153 A | * | 11/1999 | Dolan et al. |
| 6,020,210 A | * | 2/2000 | Miltenyi ..................... 436/526 |
| 6,120,856 A | * | 9/2000 | Liberti et al. |
| 6,160,087 A | | 12/2000 | Ogawa |
| 6,165,378 A | | 12/2000 | Maruno et al. |
| 6,417,011 B1 | * | 7/2002 | Miltenyi ..................... 436/526 |
| 6,562,318 B1 | | 5/2003 | Filler |
| 6,599,498 B1 | | 7/2003 | Groman et al. |
| 2004/0126902 A1 | | 7/2004 | Nishiya et al. |

OTHER PUBLICATIONS

J. Bogwald, R. Seljelid, and J. Hoffman, Carbohydrate Research, 148, 101-107 (1986).

H. Kobayashi and T. Matsunaga, Journal of Colloid and Interface Science, 141, 505-511 (1991).

Z. Xu, Q. Liu, and J.A. Finch, Applied Surface Science, 120, 269-278 (1997).

Samarendra N. Maiti, Maya P. Singh and Ronald G. Micetich, Tetrahedron Letters, 27, 1423-1424 (1986).

Jeffry S. Mann, Jin Cheng Huang, and John F.W. Keana, Bioconjugate Chemistry, 3, 154-159 (1992).

* cited by examiner

MAGNETIC PARTICLES AND METHODS OF PRODUCING COATED MAGNETIC PARTICLES

CROSS-REFERENCE TO RELATED APPLICATION

This application claims the benefit under 35 U.S.C. § 119(e) of prior provisional application No. 60/214657, filed Jun. 28, 2000, which is hereby incorporated by reference in its entirety.

FIELD OF THE INVENTION

This invention relates to a method of obtaining pure organic, inorganic, or biological materials from mixtures containing such materials. More particularly, the invention relates to a method for obtaining pure materials from such mixtures by separations using resuspendable colloidal polysaccharide-coated magnetizable particles. The invention also relates to a process for preparing the magnetizable particles used in such separations, to processes for coating the magnetizable particles, and to processes for preparing novel polysaccharide derivatives that are employed to coat the magnetizable aggregates.

The novel polysaccharide-coated magnetizable aggregates of this invention can be attached to members of specific binding pairs (msbps) with affinity for the material of interest. The polysaccharide-coated magnetizable aggregates coupled to msbps thus prepared may be used for purifications, such as, but not limited to, affinity separation, bioassays including radioimmunoassays, enzymatic assays, specific nucleic acid selection and cell selection. The polysaccharide-coated magnetizable aggregates may be used in diagnostic assays and in such therapeutic techniques as isolation of cells for use in transplantation.

Additionally, the invention provides for a kit comprising the novel polysaccharide-coated magnetizable aggregates, to which a person skilled in the art can attach msbps and use the resulting particles in purifications as described above, and also provides for a kit comprising the novel magnetizable aggregates to which msbps are already attached to be used in the above types of separations.

BACKGROUND OF THE INVENTION

The ability to conveniently separate small or large quantities of materials from mixtures with high purity and yield is crucial to many disciplines, including chemistry, biochemistry, molecular biology, immunology and cell biology, where the separation and isolation of inorganic and organic molecules and biological materials such as enzymes, nucleic acids, cells and organelles are often required.

Conventional methods for the separation of biological materials include liquid chromatography, using supports such as silica gel or agarose, gas chromatography, analytical and preparative centrifugation, electrophoresis and the like. These methods, however, are time consuming, and may require complicated, multistep procedures and complex instrumentation. Furthermore, these techniques do not readily provide aseptic materials, making the usage of the recovered materials unsuitable for therapeutic use, such as in cell transplantation. Additionally, the lengthy procedures as conventionally practiced reduce the recovery of viable cells and the stability of labile molecules.

Another method for these separations utilizes magnetic particles that are coated with msbps (members of a specific binding pair) either directly (for example U.S. Pat. Nos. 3,970,518 and 4,018,886 to Giaever) or through the intermediacy of coating materials that allow the attachment of msbps (for example, U.S. Pat. Nos. 4,230,685 to Senyei, 4,452,773 to Molday, 4,554,088 to Whitehead, 4,267,235 to Rembaum, and 4,157,323 to Yen). The msbps are chosen to have affinity for the material to be separated. Thus, by taking advantage of the magnetic properties of the particles, the materials are separated in a magnetic field (Giaever, U.S. Pat. No. 3,970,518).

Magnetic separations are superior to other separation technologies because they are rapid, non-toxic, require only simple devices and may easily be performed under sterile conditions.

Magnetic particles are most useful in separations if they meet certain criteria. They should be easily separated in a magnetic field. They should remain in uniform suspension for significant periods of time. It should be easy to attach msbps to them. There should be very little non-specific binding to the particles. The particles should be easily redispersed after the magnetic separation to facilitate the recovery of the purified material.

A wide variety of magnetic particles for use in separations have been prepared by workers in the field. The methods used to prepare the magnetic particles can be roughly divided into two types. The first method involves the coating of an existing magnetic material. The second method involves the generation of the magnetic material in the presence of the coating material. Magnetite is the most common magnetic material used, since some particles prepared from freshly precipitated magnetite are claimed to be superparamagnetic (see, for example, U.S. Pat. No. 4,827,945 to Groman), a property which facilitates resuspension of the particles after magnetic separation. Some of the patents mention the use of other magnetic materials as well. Representative examples of the first method are Giaever '518 (proteins adsorbed onto nickel microspheres), U.S. Pat. No. 4,554,088 to Whitehead (functionalized polymeric silane coating on magnetite), U.S. Pat. Nos. 5,512,332 and 5,597,531 to Liberti (adsorption of serum albumin onto aggregates of magnetite or other magnetic metal oxides during or immediately after ultrasonic disruption of the aggregates), U.S. Pat. No. 4,157,323 to Yen and U.S. Pat. Nos. 4,358,388 to Daniel (polymerization of monomers in the presence of magnetite), and 4,230,685 to Senyei (adsorption of Protein A to magnetite).

Representative examples of the second method are U.S. Pat. No. 4,452,773 to Molday (precipitation of magnetite in the presence of dextran), U.S. Pat. No. 4,795,698 to Owen (precipitation of magnetite in the presence of serum albumin), and U.S. Pat. No. 5,262,176 to Palmacci (precipitation of magnetite in the presence of arabinogalactan). A related method is the precipitation of magnetite in the pores of, or on the surface of, an existing particle, as, for example in U.S. Pat. No. 4,654,267 to Ugelstad.

The range of particle sizes available is generally limited by the method used to make the particles. Precipitation of magnetite in the presence of a coating material generally produces particles under about 50–60 nm in diameter. Coating of existing magnetic particles generally yields particles greater than 500 nm in diameter, since particles of magnetite and most other magnetic material are generally heavily aggregated under the coating conditions used. The existing particles under 50–60 nm stay suspended almost indefinitely, but can only be separated in specialized magnetic devices. Particles greater than 500 nm in diameter are easily separated magnetically, but settle out at an inconvenient rate.

Particles between 50 and 500 nm can be prepared and coated (Liberti '332 and '531) but the process used is both inconvenient and potentially injurious to the coating material. Thus there is a great need for a convenient preparation of magnetic particles for use in magnetic separations which properly combine facile magnetic separation and very slow settling rate.

Various means have been used to attach msbps to the magnetic particles. As noted above, this can be done either by direct adsorption of the msbps to the magnetic particles or by attachment of the msbps to a coating which has been placed on the magnetic particle. Proteins directly adsorbed to surfaces typically lose some of their biological activity, so most workers prefer to attach msbps to a coating that has been placed on the particle. A variety of coating materials have been used which provide a means of attaching msbps either covalently or through a strong specific binding interaction. Representative examples are described in Senyei '685 (Protein A, which allows attachment of immunoglobulins), Liberti '332 (biotinylated serum albumin, which allows attachment of avidin or streptavidin), Whitehead '088 (polymerized aminosilane, providing amino groups for covalently attachment of msbps), Rembaum '235 (polyglutaraldehyde for attachment of msbps with available amino groups), Molday '773 (dextran, which is further modified to provide aldehyde and amino groups for covalent attachment of msbps), U.S. Pat. No. 5,411,863 to Miltenyi (dextran modified with cyanogen bromide for attachment of msbps with amino or thiol groups) and U.S. Pat. No. 5,512,439 to Homes (monodisperse magnetic polystyrene beads with surface tosyloxy groups to which amine-modified nucleic acids can be attached).

In order for magnetic particles to stay in suspension for significant periods of time, they must not only have the appropriate size initially, but must also be colloidally stable, that is, they must not grow in size by aggregation. A variety of methods have been used for preparing colloidally stable magnetic particles. The two usual methods for maintaining the colloidal stability of particles are to impart a high surface charge or to coat the particle with a hydrophilic polymer. Representative examples of these two methods can be found in U.S. Pat. No. 4,329,241 to Massart (iron oxide-based magnetic fluids stabilized by the surface charge on the iron oxide surface itself), U.S. Pat. No. 4,208,294 to Khalafalla (surfactant-stabilized magnetic particles), U.S. Pat. No. 4,935,147 to Ullman (magnetic particles coated with succinylated BSA to maintain the surface charge at neutral pH), and Molday '773, Palmacci '176, and U.S. Pat. No. 4,101,435 to Hasegawa (hydrophilic polymers such as the polysaccharides dextran and arabinogalactan).

Of the coating materials which have been used, it will be noted that polysaccharides have been used as coating materials both to impart colloidal stability to the magnetic particles and to provide a means of attaching msbps to the magnetic particles. Thus, polysaccharides, and in particular dextran, appear to be particularly useful coating materials. In order to be useful, though, the msbps must be stably attached to the magnetic particle. This means that the msbps must be stably attached to the polysaccharide coating, and the polysaccharide coating must in turn be stably attached to the magnetic particle. The methods described in the literature for attaching msbps to polysaccharides, in particular, dextran, are not satisfactory. Molday '773 uses periodate oxidation of the dextran as means of introducing functional groups onto the particle surface to which msbps can be attached. Periodate oxidation, however, is known to weaken the dextran chain, and fission of the dextran chains can lead to loss of attached msbps. Miltenyi '863 describes the modification of the dextran coating with cyanogen bromide to allow attachment of msbps. It is well known from work on attachment of msbps to affinity chromatography supports that cyanogen bromide provides a labile linkage to the msbps. Thus, although polysaccharides, and dextran in particular, would be preferred coating materials for magnetic particles, polysaccharide-coated magnetic particles with stable linkages to the attached msbps have not been reported.

The stability of polysaccharide coatings attached directly to magnetic particles has not been studied extensively. When magnetite is precipitated in the presence of dextran (Molday '773) or carboxymethyldextran (U.S. Pat. No. 5,204,457 to Maruno) the attachment of the dextran to the magnetic particle appears to be stable. Simple incubation of either dextran or carboxydextran with colloidal magnetic iron oxide particles at room temperature, however, results in a labile coating. Incubation at elevated temperatures instead improves the stability, but Maruno '457 notes that carboxymethyldextran-coated magnetic particles prepared in this way have poorer stability than those prepared by precipitating magnetite in the presence of the carboxymethyldextran. As noted above, however, particles prepared by precipitation of magnetite in the presence of a coating material are typically smaller than 50–60 nm, and thus are difficult to separate magnetically. Thus, a means of stably attaching the polysaccharide coating to the magnetic particle other than incubation at elevated temperature may be needed.

Maruno '457 describes the preparation of magnetic particles coated with carboxyalkylethers of dextran, although the use of the carboxyl group for attachment of msbps is not anticipated. Attachment of msbps to a surface coated with carboxymethyldextran has been reported in B. Johnnson, et al., *Analytical Biochemistry* 198, 268 (1991). The use of carboxyalkylethers, however, is not satisfactory. Carboxymethyldextran readily forms a lactone between the carboxyl group and a hydroxy group on one of the anhydroglucose units of the dextran chain (N. D. Heindel, et. al., *Bioconjugate Chem*, 5, 98 (1994), suggesting that this hydroxyl group can catalyze the hydrolysis of any linkage between an msbps and the carboxymethyl group. The carboxyethyl groups of carboxyethyldextran can be lost via a retro-Michael reaction. Carboxyalkylethers with longer alkyl groups are expected to render the polysaccharide coating hydrophobic, leading to unacceptable non-specific binding to the particle surface. Introduction of carboxyl functionality into a polysaccharide as a means of attaching msbps would be useful. The methods which have been previously described may be adequate for some purposes, but there is still a need for a method of preparing a hydrophilic polysaccharide with pendant carboxyl groups to which msbps can be stably attached.

Accordingly, there remains a need for a convenient method for obtaining coated magnetic particles that have the following characteristics. The particles should be as small as possible in order to form stable colloidal solutions but large enough to have a significant magnetic moment, and thus be rapidly and easily separable with a small magnet. The particles must also have a large surface area to allow the binding of an amount of the material of interest in order to eliminate multi-step procedures to recover the requisite amount of material.

The coating of the aggregates also determines utility. The coating material should be stably associated with the iron core, and allow stable covalent bond formation between the coating material and the coupling molecule to allow firm attachment. It should be resistant to the non-specific binding of undesired materials present in the solution. It is preferable that the coating is non-toxic, sterilizable and preferably biodegradable to allow transplantation of the separated material directly into an animal or human patient.

An additional desirable characteristic of the magnetic particles is that they should only minimally affect the physical properties of the separated material. For example, the identity of cell populations separated with magnetic particles is conveniently analyzed by flow cytometry. Flow cytometry uses physical parameters to determine the types of cells isolated and for accurate analysis, these physical parameters must be only minimally affected by attached magnetic particles.

SUMMARY OF THE INVENTION

In a first aspect, the invention relates to a method for separating materials from mixtures containing them, comprising contacting said mixture with magnetizable particles coated with a polysaccharide having pendant functional groups to which is linked a member of a specific binding pair or coupling molecules.

In a second aspect, the invention relates to a process for the preparation of magnetizable particles coated with a polysaccharide having pendant functional groups to which are linked members of a specific binding pair or coupling molecules.

In a third aspect, the invention relates to a process for the preparation of magnetizable particles coated with a polysaccharide having pendant functional groups, comprising the steps of preparing a slurry of crystallites of magnetite by treating a solution of ferric chloride and ferrous chloride with ammonium hydroxide, aging the slurry to obtain aggregates of the desired size, fractionating the resulting magnetic aggregates by size, optionally silanizing the aggregates, and attaching a coating of a polysaccharide with pendant functional groups.

In a fourth aspect, the invention relates to a process for preparing magnetizable particles of a useful size by preparing crystallites of magnetite, aging them to aggregate them, and optionally converting them to a colloid.

In a fifth aspect, the invention relates to a process for attaching a coating of a polysaccharide with pendant functional groups to a magnetizable particle. In one embodiment, the polysaccharide is heated with the magnetizable particle. In a second embodiment, some of the pendant functional groups of the polysaccharide are linked to some of the pendant functional groups of the optional silane coating.

In a sixth aspect, the invention relates to a process for the preparation of novel polysaccharides derivatives with pendant functional groups with which to coat magnetizable particles. In one embodiment the polysaccharide derivative is a carboxypolysaccharide synthesized by a process comprising the steps of mixing the polysaccharide and sodium chloroethoxyethoxyacetate in sodium hydroxide, heating, cooling, neutralizing, and then removing salts and low molecular weight materials by washing or filtration. In a second embodiment the polysaccharide derivative is an aminopolysaccharide prepared by the steps of adding tetramethylammonium hydroxide to a solution of polysaccharide, heating the solution to 85° C., adding 1-azido-3-iodopropane and then heating to 95° C. The resulting azidopropylpolysaccharide is precipitated with methanol and purified by redissolution in water and reprecipitation with methanol. Citric acid, sodium hydroxide and stannous chloride are added to the azidopropylpolysaccharide to reduce the azido group to an amino group. The resulting aminopolysaccharide is purified by repeated precipitation with methanol.

The aminopolysaccharide may optionally be converted to bromoacetamidopolysaccharide by the reaction with the N-hydroxysuccinimide ester of bromoacetic acid.

A member of a specific binding pair, which may be antibodies, nucleic acids, biotin, digoxigenin and the like, may be conjugated to the novel polysaccharide derivatives by means known to those skilled in the art.

Another aspect of the invention is to provide a method of separating a target material from a suspension or dispersion. The method comprises the steps of combining a mass of magnetizable particles to the suspension or dispersion containing the target material for sufficient time for the target material to bind to the magnetizable particles. The magnetizable particles are formed of a particle of crystallites of a magnetizable metal oxide and have a coating of a polysaccharide derivative which has at least one pendant functional group, and a coupling group which has an affinity for the target material. A magnetic field is applied to the suspension or dispersion and the mass is separated of the magnetizable particles and target material.

Still another aspect of the invention is to provide a method of producing magnetizable particles for separation of a target material. The method comprises the steps of: providing aggregates of crystallites of a magnetizable metal oxide, coating the aggregates with a polysaccharide derivative having pendant functional groups, and coupling a coupling group to the functional group to form the magnetizable particles. The coupling group has a binding affinity for the target material and the magnetizable particles are dispersible in a liquid and are separable from a liquid by applying a magnetic field.

These aspects, advantages and other salient features of the invention will become apparent from the annexed drawing and the following detailed description of the invention.

DETAILED DESCRIPTION OF THE INVENTION

The present invention provides a novel method for producing resuspendable colloidal polysaccharide-coated magnetizable aggregates or particles to which msbps or coupling molecules are attached. The msbps or coupling molecules have an affinity for molecules associated with the materials of interest to be separated from mixtures. The polysaccharide-coated magnetizable particles are non-toxic, have a high magnetic moment and are easily attracted to simple magnets. The magnetizable particles or aggregates of this invention overcome problems associated with the size, surface area, gravitational settling rate and magnetic character of previously developed magnetic particles.

None of the prior art magnetic particles have the same composition, size, surface, surface area, coupling versatility, settling properties and magnetic behavior as the particles of the invention. The magnetizable particles of this invention are suitable for many of the assays, enzyme immobilization, cell sorting and affinity separation procedures reported in the literature and in fact, overcome many of the problems associated with particle settling and difficulty of separation experienced in the past with the use of prior art magnetic particles.

As used herein resuspendible colloidal polysaccharide-coated magnetizable aggregate or particle refers to a finely divided solid which forms a colloidal suspension, and which may be separated from the suspension by magnetic means, such as by applying a magnetic field to the suspension, and where the separated aggregates or particles can be subsequently resuspended.

The term "magnetically responsive particle or aggregate" or "magnetic particle or aggregate" or "magnetizable aggregate" or "magnetizable particle" is defined herein as any particle dispersible or suspendible in aqueous media without significant gravitational settling and is separable from suspension by application of a magnetic field, which particle comprises a magnetic metal oxide core generally surrounded by an adsorptively or covalently bound sheath or coat bearing organic functionalities to which msbps or coupling molecules can be attached. The terms "magnetizable aggregate" and "magnetizable particle" are used interchangeably.

"Magnetic" and "magnetizable" as used herein encompass materials that may or may not be permanently magnetic, including superparamagnetic, ferromagnetic, and paramagnetic materials. Superparamagnetic materials have high magnetic susceptibility and thus become magnetized in the presence of a magnetic field, but lose their magnetization when the magnetic field is removed. Ferromagnetic materials are strongly susceptible to magnetic fields and remain magnetized when the field is removed. Paramagnetic materials have only a weak magnetic susceptibility and when the field is removed quickly lose their weak magnetization.

Particles which remain strongly magnetized after exposure to a magnetic field, for example, the magnetic field used to separate them, even after removal from the magnetic field, will be strongly attracted to each other, and hence difficult to redisperse. On the other hand, after removal from the magnetic field, superparamagnetic particles are comparatively easy to redisperse, since they are not attracted to each other magnetically. It will appreciated that particles which remain weakly magnetized after removal from the magnetic field may also be comparatively easy to redisperse, so long as the thermal energy of motion (Brownian motion) is similar to or greater than the energy of magnetic interaction between the particles.

"Magnetite", $Fe_3O_4$, is a black mineral form of iron oxide crystallizing in the cubic system.

The term "metal oxide core" is defined as a crystal or aggregate of crystals of a transition metal oxide.

The term "coupling molecule" or a "msbp" (member of a specific binding pair) is defined as any biological, organic, or inorganic molecule capable of specific binding or interaction with a target material such as another biological, organic, or inorganic molecule, which binding or interaction may be referred to as "ligand/ligate" binding or interaction and is exemplified by, but not limited to, antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, repressor/inducer, nucleic acid/nucleic acid, nucleic acid/protein, nucleic acid/intercalator, or metal ion/chelate bindings or interactions.

The term "coupled magnetically responsive particle" or "coupled magnetizable particle" is defined as any magnetic particle to which one or more types of coupling molecules or msbps are either adsorbed or attached by covalent bonds, which covalent bonds may be amide, ester, ether, sulfonamide, disulfide, or other suitable organic linkages depending on the functionalities available for bonding on both the coat of the magnetic particle and the coupling molecules.

By "material of interest" or "target material" is meant any molecule, inorganic or organic, virus, organelle, or cell, nucleic acid, antigen or the like to be separated by the polysaccharide-coated magnetic aggregates of the invention.

Preferred magnetic aggregates of the invention may be made by preparing a solution of divalent ($Fe^{2+}$) and trivalent ($Fe^{3+}$) iron salts in acid and treating the resulting mixture with ammonium hydroxide to form a slurry of magnetite. Magnetite prepared in this manner consists of aggregates of small crystallites and is magnetizable. Preferably, the crystallites of the magnetizable transition metal oxides have a particle size of about 3 nm to about 25 nm. In other embodiments, the magnetizable aggregates are made from a magnetizable transition metal oxide by a similar process.

The resulting slurry of magnetite or transition metal oxide can be converted into colloidal aggregates or magnetizable aggregates of magnetizable iron oxide by treatment with either acid (perchloric acid, nitric acid, or a similar non-complexing acid), a solution of a ferric salt, such as a ferric nitrate solution, excess ferric ion (in the presence of a non-complexing counterion) or base (tetramethylammonium hydroxide or a similar non-complexing base). These treatments result in depletion of ferrous ion from the magnetite by either ion exchange or oxidation, and this depletion of ferrous ion is an important part of the formation of the colloid or magnetizable aggregates.

A preferred procedure for converting the precipitated magnetite into colloidal aggregates of a useful size has been developed. The precipitated magnetite is aged, washed with water, aged again, and then treated with ferric nitrate. The resulting material forms a colloid containing a useful fraction of aggregates above 100 nm in size, and the colloid is easily enriched in these larger particles when the colloid is purified by centrifugation.

The magnetic aggregates produced by this method are preferably between about 50 nm and about 500 nm, and typically between 100 nm and 450 nm in diameter, which provides a surface area high enough to bind many coupling molecules. The aggregates remain magnetized after exposure to a magnetic field, but the magnetization is sufficiently weak to allow facile resuspension of the aggregates after magnetic separation.

Separations of the magnetizable aggregates or particles of the invention from a dispersion only require simple magnets that generate fields of between 2,000 and 10,000 gauss, preferably between 8,000 and 10,000 gauss. Such fields can be easily obtained with permanent magnets, preferably permanent rare earth magnets. The magnets may be smaller than the container that holds the dispersion of magnetic aggregates and separated material, and, thus are suitable for benchtop use.

The magnetizable aggregates are optionally surrounded or coated by an organosilane coat that is adsorptively or covalently bound to the aggregates. Heroic efforts to polymerize and dehydrate the silane coating as described in Whitehead '088 are not necessary simple heating of an aqueous mixture of the colloid with a silanizing agent (see H. Kobayashi and T. Matsunaga, *J. Colloid. Interface Sci.*, 141, 505 (1991) and Z. Xu, et. al., *Applied Surface Science*, 120, 269 (1997) for a similar procedure, which is reported to provide roughly a monolayer silane coating) is sufficient to provide a silane coating useful for anchoring a subsequent polysaccharide coating. Preferably, the organosilane has a pendant functional group for coupling with the polysaccharide derivative. Aminopropyltriethoxysilane is conveniently used as the silanizing agent, although a variety of other silane coatings can be used, such as a glycidyloxypropyl silane or a mercaptopropyl silane, or any of the many other amino group-containing silanes which have been reported. Although colloidal aggregates form a visible suspension during the silanization reaction, the aggregates readily redisperse when the excess silanizing agent is removed, indicating that relatively little change in the size of the aggregates has occurred as a result of the silanization process.

The silanized magnetizable aggregates are coated with one or more layers of polysaccharide derivatives. In other embodiments, the magnetizable aggregates are coated directly with a polysaccharide derivative without the silane. Dextran is a readily available polysaccharide and can be used as a coating for the magnetic particles. Other polysaccharides, such as arabinogalactan, can also be used as coating materials. A functionalized dextran having a pendant functional group for coupling to a coupling group having an affinity for a target material is used for convenience, but it should be understood that other polysaccharides can be used.

A preferred dextran derivative is a carboxy dextran derivative prepared from dextran and sodium chloroethoxyethoxyacetate. The use of an oligomer of ethylene glycol as the linker between the dextran and the carboxyl function serves a dual purpose: 1) to place the carboxyl group (and thus any linkages to coupling molecules which utilize the carboxyl group) far enough away from the anhydroglucose units of the dextran to prevent hydrolysis of the linkages by the hydroxyl groups of the anhydroglucose units (as might happen if carboxymethyldextran were used as the carboxydextran); and 2) to provide a hydrophilic spacer long enough to overcome the stability problems associated with carboxymethyl and carboxyethyl ethers. Very long carboxyalkyl chains will tend to make the dextran hydrophobic and prone to non-specific adsorbtion of unwanted materials. Sodium chloroethoxyethoxyacetate is used for convenience, as it is readily prepared by oxidation of the commercially available chloroethoxyethoxyethanol, but the use of shorter or longer oligomers or polymers of ethyleneglycol is expected to provide the same benefits.

Preferably, the pendant functional group on the polysaccharide is connected to the polysaccharide by a suitable linking group, such as an oligomer of ethylene glycol. In a preferred embodiment, the linking group includes at least one heteroatom such as an oxygen atom. In one embodiment, the linking group includes at least one heteroatom for every three carbon atoms in the linking group. In other embodiments, the linking group includes at least one heteroatom for every two carbon atoms in the linking group.

The polysaccharide coating can be applied directly to the magnetic particles or to the silane coating by heating the particles in the presence of the functionalized polysaccharide. In a preferred method, the functionalized polysaccharide is covalently linked to the functionality of the silanized magnetic particles. In one embodiment, dextran can be coated directly onto the organosilane coating or directly onto the aggregates without the organosilane coating.

In another aspect the dextran derivative is an aminodextran. Aminodextrans are commonly prepared by periodate oxidation of dextran followed by reductive amination with ammonia or a diamine, treatment with epichlorohydrin followed by ammonia, treatment with aziridine or an aziridine precursor, or some similar reaction. The chemicals used in these methods can potentially weaken the dextran chain, crosslink or polymerize the dextran, or are themselves polymerizable. These problems are avoided by alkylating the dextran with a reagent that has a functionality that is convertible to an amino group and stable to the alkylating conditions. The present invention provides a method for doing this by using an azide as an amino group precursor. In one embodiment, an azidopropyl ether is formed by alkylation of dextran with 3-iodoazidopropane under basic conditions, and the azide is subsequently reduced to an amino group using stannous chloride. An additional improvement over previous procedures for the reduction of azides with stannous chloride is the provision of a complexing agent, such as a citrate buffer, in the reduction reaction mixture to maintain the solubility of the tin salts.

The aminodextran can be adsorbed directly onto the magnetic particles. In a preferred method, the magnetic particles are initially coated with a base material having functionality capable of forming stable covalent bonds with amino groups. The aminodextran is then covalently bonded to the functional group of the coating to form the aminodextran coated magnetic particles. Examples of such base coating materials are carboxydextrans and succinamidopropylsilanes.

The aminodextran can be converted to derivatized amino group, such as bromoacetamidodextran by treatment with the NHS ester of bromoacetic acid. The conversion of the amino groups to bromoacetamido groups can be complete or partial, and can be carried out before or after the aminodextran is coated onto the magnetic particle. If the conversion is carried out before the aminodextran has been coated onto the particle, the coating can be carried out as described for aminodextran, except that functional groups on the particle coating need be reactive to bromoacetamido groups, unless the conversion of amino groups to bromoacetamido groups is partial, in which case the functional groups can be reactive to either amino groups or bromoacetamido groups.

In a further aspect the magnetic particles are coated with aldehydodextran. Aldehydodextran coatings render the surface of the magnetic particle hydrophilic and in addition the aldehyde groups may be used to attach coupling molecules to the magnetic particles.

While aldehydodextran can be adsorbed onto the magnetic particle, the preferred method of attachment is via covalent bonds. For example, the aldehydodextran may be bonded to a coated magnetic particle having a coating with suitable functionality, such as an amino group, which can form an imine with the aldehyde. The imine can be optionally reduced to an amine forming a particularly stable linkage. In further embodiments, the functionalized polysaccharide can include other pendant groups such as an aldehyde group, a sulfhydryl group, and functional groups having a displaceable group, such as a halide or sulfonate. Typically, the functionalized polysaccharide includes a carboxy functional group and a linking group of a polymer or oligomer of ethylene glycol.

A wide variety of msbps or coupling groups or molecules, which capture the target material to be separated, can be covalently bonded to the silane or to the polysaccharide coating material. Examples of suitable coupling groups or coupling molecules include avidin and stretavidin. Other coupling groups having an affinity for the target material can be used. Functionality is provided on the coating materials such that any person skilled in the art can attach coupling molecules to the magnetic particle. Although the polysaccharide coating is generally to be preferred because of it hydrophilic nature, it is anticipated that in some circumstances it may be convenient to attach the coupling group or molecules directly to the silane coating, without the use of the polysaccharide coating. It is anticipated that the convenient size of the such aminosilane-coated magnetizable particles will also give to these particles properties which are superior to those particles currently available.

The resulting coated magnetic particles having a coupling group bonded to the coating can be used in immunoassays or other binding assays for the measurement of analytes in solution. Such assays preferably comprise mixing a sample containing an unknown concentration of analyte with a known amount of labeled analyte in the presence of magnetic particles coupled to msbps or coupling group or molecule capable of binding to or interacting with both unlabelled and labeled analyte, allowing the binding or interaction to occur, magnetically separating the particles, measuring the amount of labeled analyte associated with the magnetic particles and/or the amount of labeled analyte free in solution and correlating the amount of labeled analyte to a standard curve constructed similarly to determine the concentration of analyte in the sample.

Affinity separations and cell sorting can be performed using the magnetic aggregates of this invention, preferably by dispersing magnetic particles attached to coupling molecules in solutions or suspensions containing molecules or cells to be isolated and/or purified, allowing the coupling material and the desired molecules or cells to interact, magnetically separating the particles from the solutions or suspension and optionally recovering the isolated molecules or cells from the magnetic particles.

The magnetic particles of this invention are suitable for use in immobilized enzyme systems, particularly where enzyme recycling is desired. Enzymatic reactions are preferably carried out by dispersing enzyme-coupled magnetic particles in a reaction mixture containing substrate, allowing the enzymatic reaction to occur, magnetically separating the enzyme-coupled magnetic aggregates from the reaction mixture containing the product and untreated substrates and, if desired, redispersing the particles in fresh substrate thereby reusing the enzyme.

Nucleic acids can be isolated by attaching to the magnetic particles coupling molecules which interact in a sequence-specific manner with the nucleic acid of interest, such as nucleic acid binding proteins or nucleic acids with a sequence complementary to the nucleic acid of interest, or in sequence non-specific manner, such as an intercalating agent. The coupled magnetic particles prepared in this way are contacted with a mixture containing the nucleic acid of interest, allowed to interact with the nucleic acid to form a complex, and then the complex is separated magnetically from the mixture and the nucleic acid of interest is optionally released from the complex.

It is further contemplated that the magnetic particles of this invention can be used in vivo for the diagnostic localization of cells or tissues recognized by the particular coupling molecule on the magnetic particle and also for the directed delivery of therapeutic agents coupled to the particles to pathological sites.

The invention also provides a kit comprising an article of manufacture comprising a vial containing sterile or unsterile magnetic aggregates optionally coated with silane and one or more coatings of dextran or functionalized polysaccharide and one or more sterilized or unsterilized members of a sbps or coupling molecules or, packaged together, a vial contain sterile or unsterile magnetic aggregates optionally coated with silane and one or more coatings of dextran and a vial containing one or more sbps or coupling molecules.

The invention further provides a kit comprising an article of manufacture comprising a vial containing sterile or unsterile magnetic aggregates optionally coated with silane and one or more coatings of dextran

EXAMPLES

In these examples the terms "solvent", "inert organic solvent" or "inert solvent" mean a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10° C. to 50° C.; most preferably at about "room" or "ambient" temperature, (e.g., about 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, crystallization, distillation, filtration, extraction, column chromatography, solvent evaporation under reduced pressure; thin layer chromatography, thick layer chromatography, preparative low or high pressure liquid chromatography, centrifugation, electrophoresis, or a combination of these procedures. Specific illustrations of suitable separation and isolation procedures can be had by reference to the examples hereinbelow. However, other equivalent separation or isolation procedures can, of course, also be used.

Abbreviations

MES morpholinoethanesulfonic acid
MES buffer is pH 6.1 unless otherwise specified.
NHS N-hydroxsuccinimide
EDAC 1-(3-dimethyaminopropyl)-3-ethylcarbodiimide hydrochloride
SPDP 3-(2-pyridyldithio)propionic acid N-hydroxysuccinimide ester.
TCEP tris(2-carboxyethyl)phosphine
DMSO dimethylsulfoxide
DMF N,N-dimethylformamide I. Preparation of Colloidal Aggregates of Magnetizable Iron Oxide Example 1

Preparation Using Perchloric Acid Treatment

A solution prepared by diluting 71.2 g of 3.11 M ferric chloride, 16.55 g ferrous chloride tetrahydrate, and 81 mL of 1.0 M hydrochloric acid to 200 mL with water was added dropwise with agitation over a period of thirty minutes to a solution of 90 mL concentrated ammonium hydroxide in 2000 mL water. Agitation was continued for thirty minutes, then the precipitate was allowed to settle out over the course of an hour. The supernatant was drawn off, the residual slurry was divided among eight 50-mL centrifuge tubes, and the precipitate was further concentrated by centrifugation at 800×g for five minutes. The supernatant was decanted and each pellet was resuspended in 25 mL of 2 M perchloric acid. The resulting slurry was centrifuged at 800×g for five minutes. The supernatants were decanted and each pellet was resuspended in 45 mL water. The resulting colloidal dispersions were centrifuged at 1700×g for three hours. The supernatants were decanted and the pellets were resuspended in 45 mL water. The resulting colloidal dispersion was centrifuged for four minutes at 1700×g. The supernatants were centrifuged an additional twelve minutes at 1700×g. The supernatants from the twelve minute centrifugation were centrifuged for forty-five minutes at 1700×g. The pellets from the forty-five minute centrifugation were resuspended in 1.5 mL 5 mM perchloric acid each and pooled to give 14.5 mL of a colloidal dispersion of magnetizable iron oxide (62 mg/mL, 0.90 g total, 10% yield).

Example 2

Preparation of Aged Aggregates of Magnetizable Iron Oxide

A solution of iron salts was prepared by dissolving 109.78 g of ferric chloride hexahydrate, 41.37 g of ferrous chloride tetrahydrate and 17 mL of concentrated hydrochloric acid in 2400 mL of distilled water. A solution of ammonium hydroxide was prepared by dissolving 242 mL of concentrated ammonium hydroxide in 2500 distilled water. The two solutions were pumped together at room temperature over the course of 30 minutes, at the end of which time all of the iron salt solution had been used and 2310 mL of the ammonium hydroxide solution had been used. The resulting slurry of magnetite was stored at room temperature for one day. The magnetite was washed five times by drawing off the supernatant from the settled magnetite, resuspending it with 5000 mL of distilled water, and allowing it to settle again. The washed magnetite was stored for one day at room temperature before being processed further.

Example 3

Preparation of Colloidal Aggregates of Magnetizable Iron Oxide Using Ferric Nitrate Supernatant from the washed and aged magnetite from Example 2. was removed to leave a total volume of supernatant and magnetite of 600 mL. A solution of 160.1 g ferric nitrate nonahydrate in 250 mL water was added to the magnetite, the volume was made up to 1000 mL, and the magnetite and ferric nitrate solution were mixed thoroughly and stored for two hours at room temperature. The slurried aggregates of magnetizable iron oxide were washed and converted into a stable colloid by centrifuging them, decanting the supernatant, and resuspending the pellets in 5 mM perchloric acid. The washing was carried out using six 250-mL centrifuge bottles which were spun in a GSA rotor at 5000 rpm. The first centrifugation was carried out for 10 minutes, and the second and third centrifugations were carried out for 60 minutes. The pellet from the first and second centrifugations were each resuspended in 150 mL 5 mM perchloric acid. After the third centrifugation, the pellets were resuspended with a total of 500 mL of 5 mM perchloric acid to give a clear, dark reddish brown colloidal dispersion of aggregates of magnetizable iron oxide. The final volume of colloid was 520 mL, and the iron concentration was 28.3 mg/mL, giving a total of 14.7 g Fe (43% yield). A sample of the colloid was centrifuged on a sucrose gradient to estimate the size range. 80% of the aggregates had S20/w values of 2500 to 10,000, with the median being about 6500.

II. Silanization of Colloidal Aggregates of Magnetizable Iron Oxide

Example 4

Silanization of Colloidal Aggregates of Magnetizable Iron Oxide

To 500 mL of the colloidal dispersion of aggregates of magnetizable iron oxide from Example 2 was added 50 mL of aminopropyltriethoxysilane. The resulting suspension was heated at 95 C. for two hours, then cooled. The silanized aggregates were purified by centrifugation and resuspension in a 10 mM MES, pH 6.1, buffer. The reaction mixture was divided between three 250-mL centrifuge bottles and centrifuged in a GSA rotor at 5000 rpm for 10 minutes, leaving a clear light orange supernatant which was discarded. The pellets were each resuspended in 160 mL of the MES buffer. The resulting suspensions were centrifuged for 60 minutes at 5000 rpm, the supernatants were decanted and the pellets were each resuspended in 160 mL MES buffer. The silanized aggregates were washed twice more by centrifugation for 60 minute at 5000 rpm as described above. The final pellets were resuspended in a total of 480 mL MES buffer and pooled to give a stable dark, reddish brown suspension of silanized colloidal aggregates of magnetizable iron oxide, which was clear except for a slight opalescence. Large particles were removed by centrifugation at 1700×g for 6 minutes. The final volume was 500 mL and the aggregate concentration was 16.5 mg/mL as Fe, for a yield of 8.25 g Fe (59% yield). The aggregates had a median S20/w value of 10,000. The silanized aggregates were assayed for Fe and for amines and found to have 0.61 mmole amine per mg Fe. A sample of the material was dried. The dried material had a saturation magnetization of 64.1 emu/g, a remanent magnetization of 0.91 emu/g, and a coercive force of 7 Oe.

III. Fractionation of Colloidal Aggregates of Magnetizable Iron Oxide According to Size of Aggregate Example 5

Fractionation of Colloidal Aggregates of Magnetizable Iron Oxide According to Size of Aggregate The size of the aggregates left in the supernatants after centrifugation during the purification of the aggregates was compared with the size of the aggregates in the final colloidal dispersions of both the aggregates of magnetizable iron oxide from Example 3 and the silanized aggregates from Example 4. The aggregates in the second and third supernatants in Example 3 had median Sw/20 values of 2500 and 5000, as compared with a median of 6500 for the aggregates in the final colloidal dispersion. Similarly, the silanized aggregates in the third and fourth supernatants in Example 4 had median Sw/20 values of 4000 and 6000, as compared with a median of 10,000 for the silanized aggregates in the final colloidal dispersion

IV. Preparation of Dextran Derivatives

Example 6

Preparation of Carboxydextran from Dextran and Sodium Chloroethoxyethoxyacetate 10.19 g of dextran (weight average molecular weight 70,000) was dissolved in 40 mL water. 1.6 mL of a solution made from 0.3 g sodium borohydride and 1.5 mL of 10 M sodium hydroxide was added and the solution was stirred for 15 minutes. 40 mL of a 0.91 M solution of sodium chloroethoxyethoxyacetate was added, followed by 8 mL of 10 M sodium hydroxide, and the resulting solution was heated with stirring at 95° C. for 6 hours. The solution was cooled and excess base was neutralized with 1 M hydrochloric acid. Salts and low molecular weight materials were removed by continuous washing using a 50,000 weight average molecular weight cut-off hollow fiber filter. The carboxyl group content was determined by acid-base titration, and the dextran concentration was determined using anthrone/sulfuric acid. The degree of substitution was 0.11 carboxyl group per anhydroglucose unit. The yield was 7.1 g of carboxydextran.

Example 7

Preparation of Aminodextran 5.11 g dextran (average molecular weight 70,000) was dissolved in 25 ml water. 12.5 ml of 25% tetramethylammonium hydroxide in water was added, followed by dropwise addition of 75 ml of DMSO. The solution was heated to 85° C., during which time a total of 4.0 ml of 1-azido-3-iodopropane (prepared from 1-bromo-3-chloropropane by reaction with sodium azide in aqueous DMF, followed by treatment with potassium iodide in DMF) was added. The mixture was then heated at 95° C. for 1 hr.

The azidopropyldextran was precipitated with methanol and purified by repeated redissolution in water and reprecipitation with methanol, and finally dissolved in 50 ml of water. To this aqueous solution of azidopropyldextran was added 10 g citric acid, 5.0 ml 10 M sodium hydroxide, and an additional 50 ml of water. To the citrate-buffered solution of azidopropyldextran was added 5.0 ml of 1 M stannous chloride. Bubbles formed immediately. After 30 minutes, no further bubbling was observed. An additional 5.0 ml of 1 M stannous chloride was added and a small amount of additional bubbling ensued. 30 minutes after the second addition, the aminodextran was purified by repeated precipitation from an aqueous solution with methanol. The aminodextran was assayed for dextran with anthrone in sulfuric acid and for amino groups with trinitrobenzenesulfonic acid, and found to have a degree of substitution of 0.075 amino groups per anhydroglucose unit.

V. Preparation of Magnetizable Aggregates Coated with Dextran Derivatives

Example 8

Direct Coating of Colloidal Aggregates of Magnetizable Iron Oxide with Carboxydextran 0.64 mL of a 62 mg/mL dispersion of colloidal aggregates of magnetizable iron oxide prepared as in Example 1, 1.86 mL of 5 mM perchloric acid, and 2.50 mL of an 85 mg/mL solution of carboxydextran prepared as in Example 6 (degree of substitution 0.08) were mixed and heated at 90–95° C. for two hours. The coated aggregates were freed from excess dextran by centrifugation and resuspension of the pellets in 10 mM MES buffer. The first centrifugation was for 135 minutes, the second and third for 90 minutes, all at 1700×g. The dispersion of aggregates was freed from large particles by centrifugation at 1700×g for 4 minutes, giving 12 mL of a colloidal dispersion of carboxydextran-coated magnetizable aggregates containing 4.18 mg/mL Fe, with a dextran content of approximately 0.25 mg/mg Fe.

Example 9

Coating of Silanized Colloidal Aggregates of Magnetizable Iron Oxide with Carboxydextran To a solution of 3.00 g carboxydextran (prepared as in Example 6, degree of substitution 0.11) in 150 mL of 4 mM MES, pH 6.1 was added 150 mL of a 6.6 mg/mL dispersion of silanized colloidal aggregates of magnetizable iron oxide (prepared as in Example 4) in 10 mM MES, pH 6.1. The resulting mixture was stored overnight at room temperature. A solution of 1.37 g N-hydroxysuccinimide and 6.41 g EDAC in 25 mL water was then added, and the reaction mixture was stored overnight at room temperature. The carboxydextran-coated magnetizable aggregates were purified as described below. The coated aggregates were assayed for dextran and Fe and found to have 0.24 mg dextran per mg Fe. A dried sample was found to have a saturation magnetization of 55 emu/g, a remanent magnetization of 1.17 emu/g, and a coercive force of 8 Oe. The carboxydextran-coated magnetizable aggregates prepared in this manner were shown by dynamic light scatter to have a volume-weighted average diameter of 190+−60 nm. Examination of an electron micrograph of the coated aggregates revealed that the aggregates were irregular clusters of crystallites, and that the crystallites had diameters ranging from about 5 to 20 nm.

Example 10

Colloidal Stability of Carboxydextran-Coated Magnetizable Aggregates

Samples of colloidal aggregates of magnetizable iron oxide, silanized colloidal aggregates of magnetizable iron oxide, and carboxydextran-coated magnetizable aggregates prepared as in Example 9 were each added to test tubes containing 1.0 M sodium phosphate buffer, pH 6.8. The colloidal aggregates of magnetizable iron oxide flocculated immediately. The silanized aggregates of magnetizable iron oxide flocculated in less than a minute. The carboxydextran-coated magnetizable aggregates showed no sign of flocculation after three days at room temperature.

Example 11

Preparation of Aminodextran-Coated Magnetizable Aggregates mL of an aqueous solution containing 20 mg of the aminodextran from Example 7 is added to 1.0 mL 10 mM MES buffer containing 20 mg of the purified carboxydextran-coated magnetizable aggregates from Example 9, and the mixture is stored at room temperature for 24 hours. A solution of 10 mg N-hydroxysuccinimide and 40 mg EDAC in 0.2 mL water is added and the solution is stored overnight at room temperature. The aminodextran-coated magnetizable aggregates are purified as described below.

Example 12

Preparation of Bromoacetamidodextran-Coated Magnetizable Aggregates 0.5 mL of a 50 mg/mL solution in DMF of the N-hydroxysuccinimide ester of bromoacetic acid is added to 5.0 mL of 0.5 M sodium phosphate, pH 7.5, containing 100 mg of the purified aminodextran-coated magnetizable aggregates from Example 11. The reaction mixture is stored overnight at room temperature and then purified by magnetic separation as described below.

Example 13

Preparation of Aldehydodextran-Coated Magnetizable Aggregates 1.0 mL of an aqueous solution containing 20 mg aldehydodextran, with a degree of substitution of 0.1 (prepared, for example, as described in *Carbohydrate Research*, 148, 101 (1986)), is added to 1.0 mL of the dispersion of silanized colloidal aggregates of magnetizable iron oxide from Example 4, and the resulting mixture is stored at room temperature for 24 hours. A freshly prepared solution of 5 mg of freshly recrystallized sodium cyanoborohydride in 1 mL of 0.3 M MES buffer is added and the solution is stored overnight at room temperature. The resulting aldehydodextran-coated magnetizable aggregates are purified by magnetic separation as described in Example 14.

Example 14

Purification of Carboxydextran-Coated Magnetizable Aggregates

The carboxydextran-coated magnetizable aggregates prepared in Example 9 were purified by drawing them to the sides of a 13×100 test tube with a pair of 0.15"×0.32"×1.00" iron-neodymium-boron magnets placed on either side of the test tube, removing the supernatant, and redispersing the "magnetic pellet" in fresh 10 mM MES buffer. This process was carried out four times.

VI. Attachment of Coupling Molecules to Aggregates of Magnetizable Aggregates Coated with Dextran Derivatives

Example 15

Attachment of Streptavidin

To 9.1 mL of 10 mM MES buffer containing 10 mg of carboxydextran-coated magnetizable aggregates prepared as in Example 9 was added a solution of 40 mg N-hydroxysuccinimide and 200 mg EDAC in 0.8 mL water and stored at room temperature for 15 minutes. The activated aggregates were freed from excess NHS and EDAC by a total of two magnetic separations as described in Example 14. A solution of 10 mg streptavidin in 1.0 mL 0.1 M sodium phosphate, pH 7.7, was added and the solution was stored overnight at room temperature. The resulting streptavidin-labeled magnetizable aggregates were purified using three magnetic separations as described in Example 14. The streptavidin-labeled magnetizable aggregates were shown by a biotin-binding assay to be labeled with 20 mg streptavidin per mg Fe.

Example 16

Attachment of Oligonucleotide Complementary to Lambda gt11 DNA 1 mg of the oligonucleotide d(TTG ACA CCA GAC CAA CTG GTA ATG), complementary to lambda gt11 DNA, is synthesized and purified by standard methods on an Applied Biosystems nucleic acid synthesizer substituting N-linker-C-amidite (Sigma, catalog number L1909) for the C at the fifth position. The modified oligonucleotide is dissolved in 0.5 mL of 0.1 M sodium phosphate, pH 7.5, and treated with 0.1 mL of DMF containing 5 mg of SPDP. The reaction mixture is stored overnight, and then the derivatized oligonucleotide is purified by precipitation with ethanol. The derivatized oligonucleotide is taken up in 0.5 mL 0.1 M sodium phosphate buffer, pH 7.5, and treated in an argon atmosphere with a solution of 5 mg TCEP in 0.5 mL of the same buffer to reduce the disulfide to a mercaptan. The mercaptan-derivatized oligonucleotide is purified by precipitation with ethanol, taken up in 0.5 mL of 0.1 sodium phosphate buffer, pH 7.5, in an argon atmosphere and added to 5 mg bromoacetamidodextran-coated magnetizable aggregates prepared as in Example 12 in 0.5 mL of 0.1 M sodium phosphate buffer. The mixture is stored overnight at room temperature under argon, then treated with 0.1 mL of 0.1M sodium mercaptoacetate to cap residual bromoacetamido groups. The oligonucleotide-labeled magnetizable aggregates are purified by magnetic separation as described in Example 14.

Example 17

Attachment of Anti-CD4 Antibody 1 mL of a 1 mg/mL solution of mouse anti-CD4 antibody (Sigma C-1805) in 10 mM MES buffer is added to 1 mL of 10 mM MES buffer containing 5 mg of aldehydodextran-coated magnetizable aggregates prepared as in Example 13. The mixture is stored at room temperature for 24 hours. A solution of 5 mg of freshly recrystallized sodium cyanoborohydride in 1 mL of 0.3 M MES, pH 6.1, is added to the mixture, and the resulting mixture is stored overnight at room temperature. The resulting anti-CD4-labeled magnetizable aggregates are purified by magnetic separation as described in Example 14.

Example 18

Attachment of Digoxigenin

To a solution of 3.00 g carboxydextran (prepared as in Example 6, degree of substitution 0.11) in 150 mL of 4 mM MES, pH 6.1 was added 150 mL of a 6.6 mg/mL dispersion of silanized colloidal aggregates of magnetizable iron oxide (prepared as in Example 4) in 10 mM MES, pH 6.1. The resulting mixture was stored overnight at room temperature. A solution of 1.37 g N-hydroxysuccinimide and 6.41 g EDAC in 25 mL water was then added, and the reaction mixture was stored overnight at room temperature. The carboxydextran-coated magnetizable aggregates were purified as described below. The coated aggregates were assayed for dextran and Fe and found to have 0.24 mg dextran per mg Fe. A dried sample was found to have a saturation magnetization of 55 emu/g, a remanent magnetization of 1.17 emu/g, and a coercive force of 8 Oe. The carboxydextran-coated magnetizable aggregates prepared in this manner were shown by dynamic light scatter to have a volume-weighted average diameter of 190 nm, S.D. =60 nm. Examination of an electron micrograph of the coated aggregates revealed that the aggregates were irregular clusters of crystallites, and that the crystallites had diameters ranging from about 5 to 20 nm.

VII. Utility of Dextran-Coated Magnetizable Aggregates with Attached Coupling Molecules Example 19

Isolation of Lambda gt11 DNA

*E. coli* Y1090 which has been infected with lambda gt11 is lysed using lysozyme followed by Triton X-100, and the resulting mixture is treated with proteases. To 1.0 mL of the treated lysate is added 0.1 mL of a 1 mg/mL suspension of the oligonucleotide-labeled magnetizable aggregates from Example 16. The mixture is heated to 90° C., treated with 0.1 mL of 1 M sodium chloride and cooled to room temperature. The magnetizable aggregates are separated from the solution with a magnet and washed three times with a 10 mM MES, 0.1 M sodium chloride, pH 6.1, buffer by resuspending the magnetizable aggregates in 1.0 mL buffer and separating them again magnetically. The separated aggregates are finally resuspended in 1.0 mL deionized water to allow the lambda gt11 DNA hybridized to the aggregates to dissociate. The magnetizable aggregates are separated from the solution magnetically, leaving a solution of substantially purified lambda gt11 DNA.

Example 20

Isolation of CD4-Positive T-Cells

A suspension of $2 \times 10^8$ T-cells in 1.0 mL of PBS containing 3% fetal calf serum and 0.1% sodium azide is treated with 1.0 mL of a 1 mg/mL suspension of the anti-CD4-labeled magnetizable aggregates from Example 17. The mixture is incubated at 4 C. for 20 minutes, after which the complexes formed between the anti-CD4-labeled magnetizable aggregates and CD4-positive T-cells are separated magnetically. The separated complexes are resuspended in PBS buffer and separated magnetically once again. After the final resuspension in PBS buffer, the cells are counted and analyzed by flow cytometry. The CD4-positive cells are found to be recovered in 95% yield, and are 90% pure.

Example 21

Assay for Digoxin 0.10 mL of a serum sample which may contain digoxin is added to 1.00 mL of a solution of fluorescein-labeled Fab fragments of anti-digoxin antibody containing 0.3 nM digoxin binding sites. The resulting solution is incubated 5 minutes at room temperature, after which time 0.1 mL of a 1 mg/mL suspension of the digoxigenin-labeled magnetizable aggregates from Example 14 is added. The mixture is incubated an additional 5 minutes at room temperature, at the end of which time the magnetizable aggregates are separated magnetically. A portion of the supernatant is removed and the fluorescence intensity of the solution is measured. The fluorescence intensity is corrected for any fluorescence resulting from the sample itself by measuring the fluorescence of a sample treated as above, but using unlabeled anti-digoxin. The digoxin concentration in the serum sample is determined by comparing the corrected fluorescence intensity with the corrected fluorescence intensity observed when standards containing 0, 0.5, 1, or 2 ng/mL digoxin in serum are analyzed as above.

Example 22

Depletion of CD4- and CD8-Positive Cells from a Leucocyte Preparation

A sample of blood is subjected to hypotonic lysis, then centrifuged to yield a pellet containing leucocytes substantially free of erythrocytes. The leucocytes are resuspended in PBS containing 3% fetal calf serum, then cooled to 4° C. To 1.0 mL of this suspension is added 5 mL of a solution in PBS which contains 1 mg/mL each of a biotinylated anti-CD4 antibody and a biotinylated anti-CD8 antibody. The suspension is mixed and incubated for twenty minutes, at the end of which time 1.0 mg of the streptavidin-labeled magnetizable aggregates from Example 15 dispersed in 1.0 mL of MES buffer is added. The resulting mixture is incubated for twenty minutes at 4° C. The complexes formed between the streptavidin-labeled magnetizable aggregates and the cell labeled by the biotinylated anti-CD4 antibodies and the biotinylated anti-CD8 antibodies are separated magnetically, leaving a suspension of leucocytes substantially depleted of CD4- and CD8-positive cells.

While various embodiments have been chosen to demonstrate the invention, it will be understood by those skilled in the art that various modifications and additions can be made without departing from the scope of the invention as defined in the appended claims.

What is claimed is:

1. A method of separating a target material from a liquid mixture, comprising:
    forming and at least substantially purifying aggregates having a plurality of crystallites of a magnetizable metal oxide;
    coating the formed and at least substantially purified aggregates with a polysaccharide material to form coated aggregates, wherein the polysaccharide material includes at least one pendant carboxyl group directly attached to a linker which is directly attached to a polysaccharide, wherein the linker has at least one heteroatom for every three carbon atoms in the linker;
    treating the coated aggregates by attaching a specific binding member having a binding affinity for the target material to the polysaccharide material via the carboxyl group to form treated aggregates;
    combining the treated aggregates with the liquid mixture containing the target material for a sufficient time for the target material to bind to the specific binding member;
    applying a magnetic field to the combination of the treated aggregates and the liquid mixture; and
    separating the treated aggregates, including the target material bound thereto, from the liquid mixture, using the magnetic field.

2. The method of claim 1, wherein the target material is an inorganic material, an organic compound, or a biological material.

3. The method of claim 1, wherein the crystallites have a particle size of about 3 nm to about 25 nm.

4. The method of claim 1, wherein the formed and at least substantially purified aggregates have a particle size of about 70 nm to about 450 nm.

5. The method of claim 1, wherein the magnetizable metal oxide is a magnetizable iron oxide.

6. The method of claim 1, wherein the step of forming aggregates of crystallites includes a step of aging the crystallites to increase the size of the aggregates, prior to the step of purifying.

7. The method of claim 1, wherein the step of forming aggregates of crystallites includes a step of treating precipitated magnetite with an acid, with a solution of a ferric salt, or with a base to form a colloidal suspension.

8. The method of claim 1, wherein the step of forming aggregates of crystallites includes a step of treating precipitated magnetite with a reactant selected from the group consisting of nitric acid, perchloric acid, a solution of ferric nitrate, and tetramethylammonium hydroxide.

9. The method of claim 1, wherein the step of coating the aggregates includes a step of bonding the polysaccharide material directly to the aggregate of crystallites of the magnetizable metal oxide.

10. The method of claim 1, wherein the step of coating the aggregates includes steps of bonding an organosilane directly to the aggregate of the crystallites, and bonding the polysaccharide material to the organosilane.

11. The method of claim 10, wherein the step of bonding a polysaccharide material to the organosilane includes a step of attaching the polysaccharide material to a pendant functional group on the organosilane.

12. The method of claim 1, wherein the step of combining the aggregates with the liquid mixture includes a step of dispersing the aggregates in the mixture.

13. The method of claim 1, further comprising:
dissociating the treated aggregates and the target material, after the step of separating, so that they no longer are bound to one another; and
removing the treated aggregates using a magnetic field to provide a substantially pure preparation of the target material.

14. The method of claim 1, wherein the heteroatom of the linker is oxygen.

15. The method of claim 1, wherein the linker is derived from ethylene glycol, an oligoethylene glycol, or a polyethylene glycol.

16. The method of claim 1, wherein the polysaccharide is dextran.

17. The method of claim 1, wherein the specific binding member is selected from the group comprising an antibody, a nucleic acid, an enzyme, a ligand, an epitope, a binding protein, and a chelate.

18. The method of claim 1, wherein the specific binding member is an antibody, a nucleic acid, biotin, or digoxigenin.

19. A method of separating a target material from a liquid mixture, comprising:
forming and at least substantially purifying aggregates of two or more crystallites of a magnetizable metal oxide;
coating the formed and at least substantially purified aggregates with a polysaccharide material to form coated aggregates, wherein the polysaccharide material includes at least one pendant carboxyl group attached to the polysaccharide through a linker having at least one heteroatom for every three carbon atoms in the linker, wherein the pendant carboxyl group is introduced by reaction with chloroethoxyethoxyacatic acid and base;
attaching a coupling group having an affinity for the target material to the polysaccharide material via the carboxyl group, to form treated aggregates;
combining the treated aggregates with the liquid mixture containing the target material for a sufficient time for the target material to bind to the polysaccharide material;
applying a magnetic field to the combination of the treated aggregates and the liquid mixture; and
separating the treated aggregates, including the target material bound thereto, from the liquid mixture, using the magnetic field.

* * * * *